United States Patent [19]

Fisher et al.

[11] Patent Number: 4,829,839
[45] Date of Patent: May 16, 1989

[54] METHOD FOR DETERMINING THE ENVIRONMENTAL STRESS CRACKING RESISTANCE OF PLASTIC ARTICLES

[75] Inventors: James H. Fisher, Wheaton; Philip Jacoby, Naperville, both of Ill.

[73] Assignee: Amoco Corporation, Chicago, Ill.

[21] Appl. No.: 202,113

[22] Filed: Jun. 3, 1988

Related U.S. Application Data

[62] Division of Ser. No. 895,892, Aug. 12, 1986, Pat. No. 4,750,369.

[51] Int. Cl.$^4$ ............................................. G01N 33/44
[52] U.S. Cl. ............................................ 73/866; 436/2
[58] Field of Search ........................ 73/838, 799, 866; 436/2, 5, 6

[56] References Cited

U.S. PATENT DOCUMENTS

| | | | |
|---|---|---|---|
| 2,506,048 | 5/1950 | Van den Akker | 73/852 |
| 2,966,792 | 1/1961 | Di Pieri | 73/838 X |
| 3,710,616 | 1/1973 | Smith et al. | 73/838 X |
| 4,107,979 | 8/1978 | Saeda et al. | 73/799 X |
| 4,122,131 | 10/1978 | Bussink et al. | 525/89 |
| 4,230,831 | 10/1980 | Sakurai et al. | 525/240 |
| 4,371,663 | 2/1983 | Russell | 525/72 X |
| 4,390,666 | 6/1983 | Moriguchi et al. | 525/194 |
| 4,550,156 | 10/1985 | Gallagher | 528/125 X |
| 4,750,369 | 6/1988 | Fisher et al. | 73/838 X |

FOREIGN PATENT DOCUMENTS 150507  9/1981  German Democratic Rep. .... 436/2

OTHER PUBLICATIONS

Technical Note: "A New Accelerated Test for Studying the Susceptibility of Stainless Steels to Chloride Stress Corrosion Cracking"; *Corrosion (USA)*; vol. 35, No. 9, pp. 429-431; Stare Henrikson et al.

*Primary Examiner*—Tom Noland
*Attorney, Agent, or Firm*—Maria Parrish Tungol; William H. Magidson; Ralph C. Medhurst

[57] ABSTRACT

A method and device are disclosed for the determination of the environmental stress crack resistance (ESCR) of polymer articles made from polymers such as acrylonitrile-butadiene-styrene copolymers, polycarbonate, polystyrene and blends thereof. The method and device involve the external application of stress to an unstressed test article which has been exposed to a stress cracking agent. The stress is induced by means of a weight located below the horizontal plane of the plastic article. The time between the application of stress and the cracking of the test article is measured to compute a characteristic ESCR parameter and thereby evaluate the environmental stress crack resistance of the article.

8 Claims, 2 Drawing Sheets

METHOD FOR DETERMINING THE ENVIRONMENTAL STRESS CRACKING RESISTANCE OF PLASTIC ARTICLES

This is a division of application Ser. No. 895,892, filed Aug. 12, 1986, and now U.S. Pat. No. 4,750,369.

BACKGROUND OF THE INVENTION

This invention relates to a method and device for measuring the environmental stress crack resistance of plastic articles.

An important aspect of the production and use of plastic articles is the evaluation of physical characteristics of articles made from plastics. Besides having applications in engineering and design, the data obtained from such evaluations may be used to monitor the quality of the plastic produced and the products thereof or to set specifications for acceptance testing of raw materials. It is known that certain polymers are sensitive to stress-cracking in the presence of certain chemical agents. For example, high impact polystyrene (HIPS), copolymers of acrylonitrile butadiene and styrene (ABS), and high impact polyvinyl chlorides are sensitive to stress-cracking in the presence of oils. Such an effect is known as "environmental stress cracking" or "environmental stress fracture." In the presence of stress cracking agents, plastic articles can undergo stress failure (cracking or crazing) at stress levels below those which would otherwise induce such failure. Evaluation of the ability of a particular plastic article to resist such environmental stress cracking is important since the end use of such a product may involve contact with certain materials known to promote stress cracking. Methods for evaluating environmental stress cracking have also been used in fundamental studies of polymer properties and behavior. It has been observed that certain polymer characteristics such as molecular weight and morphology affect the tendency of the plastic article to undergo environmental stress cracking.

An article by Titow in *Plastics and Polymers* (June 1975) discloses the known methods for determining the tendency of plastic articles to undergo environmental stress cracking. Tensile-load methods are known, including the so-called Lander test (ASTM D-2552) in which twenty waisted tensile specimens are immersed in a liquid medium under constant tensile load. Other tensile-load methods involve a specimen with a hole in the center held at constant tension.

Another device for measuring the tendency of plastic articles to fail under stress is disclosed by Haslett et al. in the SPE Journal (March 1964). The weight which produces the load on the specimen is located above the horizontal plane of the specimen. The disclosed device requires a ball bearing bushing to reduce the air friction of the loading shaft and an air cylinder to absorb the shock of weight's fall after fracture, while at the same time actuating a normally closed pressure switch to the timer to record the exact time of failure.

An apparatus for measuring flexural creep rupture is disclosed by Schmitz et al. in SPE, 17th ANTEC, Volume VII (January 1961). A beam is loaded with a weight from above in the center of a four-inch span. The apparatus records failure times automatically by means of a micro switch which is tripped after the bearing rod has moved 2.5 inches.

U.S. Pat. No. 3,710,616 to Smith et al. discloses an apparatus and method wherein a weighted rod stresses a plastic article in contact with a stress cracking agent and an electrically conductive liquid until the liquid penetrates the stress cracks which appear. Another method for measuring the environmental stress cracking of plastic materials is disclosed by Sieda et al. in U.S. Pat. No. 4,107,979 wherein the test piece is initially deformed in a test environment and an additional stress of a magnitude smaller than that of the stress already produced in the test piece is applied until the test piece fractures. The apparatus requires a means for placing the test piece under stress before the test begins.

A creep testing apparatus is disclosed in U.S. Pat. No. 2,506,048 to Van den Akker. The disclosed apparatus includes means for subjecting a test specimen to a tensional or flexural load over a prolonged period of time. At various intervals during the loading period, the deflection of the material is measured. The load is applied by a weight pan attached to a loading yoke which causes a weight distributing bar to apply the load to the specimen. The weight pan is located below the horizontal plane of the specimen.

The devices of the prior art are relatively large so that multiple testing units can occupy an inconvenient amount of space in a plant situation. Further, required components such as a significant amount of conductive liquid, means for initially deforming a test specimen and means for accurately measuring the deflection of a specimen make the prior art methods and devices inconvenient for quick, successive tests on a routine basis. When the weight producing the load is located above the horizontal plane of the test specimen, additional means are needed to maintain the weight in a fixed path and minimize friction so that successive test conditions can be duplicated for meaningful results.

It is an object of this invention to provide a sensitive method of measuring the environmental stress crack resistance (ESCR) of plastic articles which has a high level of reproducibility and a short turnaround time.

Another object of this invention is to provide a device for measuring the ESCR of plastic articles which is convenient to use and produces accurate, reproducible results.

SUMMARY OF THE INVENTION

The method of this invention comprises contacting one side of a plastic article with a chemical stress crack agent, applying a uniform stress to the opposite side of said article by means of a weight located below the horizontal plane of said article, and recording the time elapsed between the application of stress and the failure of the article detected by the vertical displacement of said weight.

The device for performing the method comprises a means for supporting the device, means for supporting at least one test article, transfer means for applying a load to said article, means for producing said load located below the horizontal plane of said transfer means and said article, means for detecting the displacement of said transfer means. The device can also include a means for measuring the time elapsed between the initial application of stress to said article and the subsequent displacement of said transfer means due to the failure of said article wherein said measuring means is connected to said detecting means.

According to this invention, there is provided a testing device comprising a support frame comprising a horizontal base having a vertical arm on each end; a test article support comprising a horizontal platform having two vertical panels attached to the outer edges of the upper face of said platform wherein at least one of said panels has at least one opening, a horizontal member connecting the upper edges of said panels, said platform and said member each having at least one opening in vertical alignment with an opening in the other, two vertical holders connected to the outer edges of the upper face of said member; a hanger assembly comprising a frame, a vertical connector attached to the bottom of said frame, and a horizontal lever attached to said connector for moving said assembly in a vertical direction wherein said connector is aligned so as to pass freely through the openings in said platform and said horizontal member and said lever is aligned to extend through the opening in said panel; a weight connected to said assembly wherein said weight is located below said platform; means for detecting the vertical displacement of said assembly; means for measuring the time elapsed between the hanging of said assembly and weight on the test article and the vertical displacement of said assembly.

BRIEF DESCRIPTION OF THE DRAWINGS

In the accompanying drawings:

FIG. 3 shows an end-on view of the device of this invention.

DETAILED DESCRIPTION OF THE INVENTION

Figure 1:
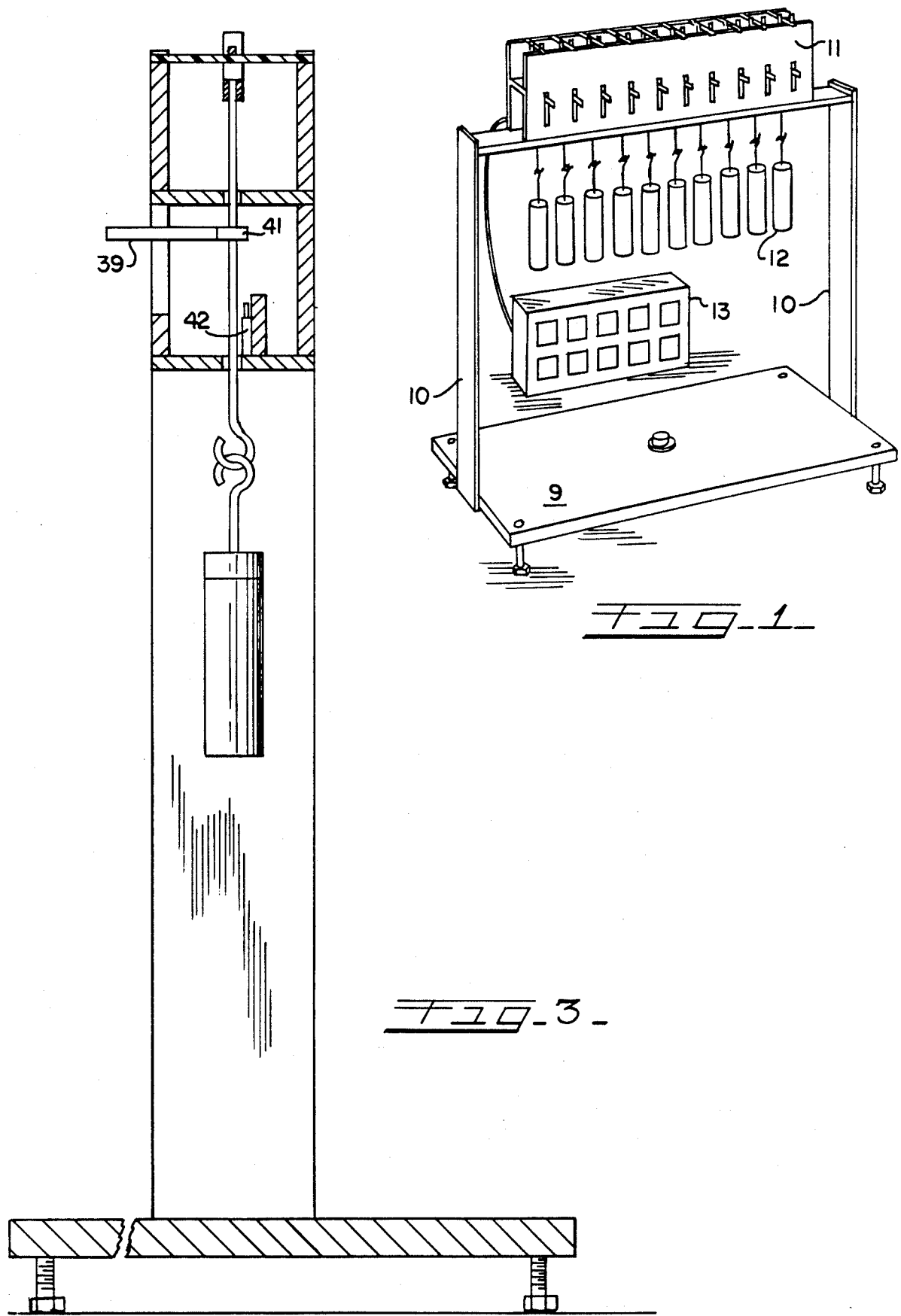
FIG. 1 shows a view of an embodiment of the device capable of performing several tests simultaneously.

The present invention is described in detail as a method and device for measuring the environmental stress crack resistance of plastic articles with the understanding that the detailed description is to be considered an illustration of the principles of the invention and is not intended to limit the invention to the embodiment illustrated. The method and device of the present can be used wherever it is necessary to measure the resistance of a plastic article to cracking in the presence of a hostile environment.

The method and device of this invention provide a sensitive and convenient means of obtaining reproducible data on the ESCR of plastic articles. The method provides a means of ranking and quantifying the tendency of articles made from certain polymers such as high impact polystyrene, to develop catastrophic cracks when place under stress in the presence of a stress cracking agent. Besides being an important property for many end-use applications, the ESCR of a particular polymer can also be correlated with several important variables. For example, high impact polystyrene (HIPS) resins are graft blends of rubber and polystyrene. The ESCR of test articles made from such resins can be correlated with variables such as the rubber particle size, the rubber level, the polystyrene molecular weight, plasticizer type and level as well as the degree of grafting between the rubber and polystyrene phases. For example, low ESCR results were observed when these variables were decreased.

The improvement of ESCR in thermoplastic resins requires an understanding of how these variables affect ESCR. The method and device of this invention provides a reproducible measure of the ESCR which is essential in acquiring such an understanding. On a practical level, the method and device of this invention can be used at a plant to monitor certain product characteristics so that upsets during polymerization can be detected and corrected. In a plant situation, one would like to know when a key process or product variable has changed so that it can be adjusted and any off-spec material segregated from prime material. Once a target ESCR is established, the method and device can also be used to identify both incoming and outgoing material which does not conform to the desired specifications. It is important that the method and device for determining the ESCR of a plastic material be convenient to use for quick successive sampling while producing accurate, reproducible results.

The method of this invention is applicable to plastic articles which exhibit an increased tendency to crack in the presence of a hostile environment. Such articles include those formed from amorphous polymeric materials such as polystyrene, acrylonitrile-butadiene-styrene copolymers, polycarbonates and blends of polystyrene such as polystyrene/polyphenylene oxide blends. The method and device of this invention are particularly useful in testing articles made from HIPS resins, acrylonitrile-butadiene-styrene (ABS) copolymers and rigid polyvinyl chlorides.

The hostile environment in which the article is tested can be a liquid, solid, or gaseous. Examples of stress cracking agents useful in the method of this invention include fats, oils, greases, and organic solvents such as aromatic hydrocarbons. Articles made from HIPS and ABS polymers are known to be susceptible to cracking when contacted with oleic acid or vegetable oils. Butter and margarine can be used as stress cracking agents in the process of this invention.

Having the weight which produces the load on the test article below the plane of the article reduces the number of components necessary in a device to measure ESCR. When the weight is above the plane of the test article, other factors such as torque and friction come into play since the weight will have a tendency to rotate and will experience friction with the elements needed to hold it in a fixed path. In the device of this invention, stress is applied to the test article by an assembly which is freely hanging on an otherwise unstressed article. When the article experiences catastrophic cracking, the assembly and the weight drop and their displacement marks the time of failure of the article. The ESCR for the polymer material being tested is expressed herein as an average failure time of its molded articles when subjected to a constant flexural stress while in contact with a stress cracking agent. The method and device of this invention can be readily automated so that multiple tests can be performed and the results recorded automatically.

Referring more specifically to the drawings, FIG. 1 illustrates an embodiment of the invention showing the entire device including the timer assembly. The support frame comprises a horizontal base 9 which is connected at either end to the end of two vertical arms 10. The test article support 11 is suspended between said arms. The weight 12 producing the load hangs freely below the test article support. The timer assembly 13 is used to measure the time between the application of stress to the test article and the catastrophic cracking of the article. The timer need not be directly connected to the testing device. In a manual testing method, the displacement of the hanger assembly could be detected by sight or sound and the time noted on a separate timer. However, an advantage in using a connected timer is the ability to automate the testing so that it does not depend on sight or sound and several tests can be run and monitored simultaneously.

Figure 2:
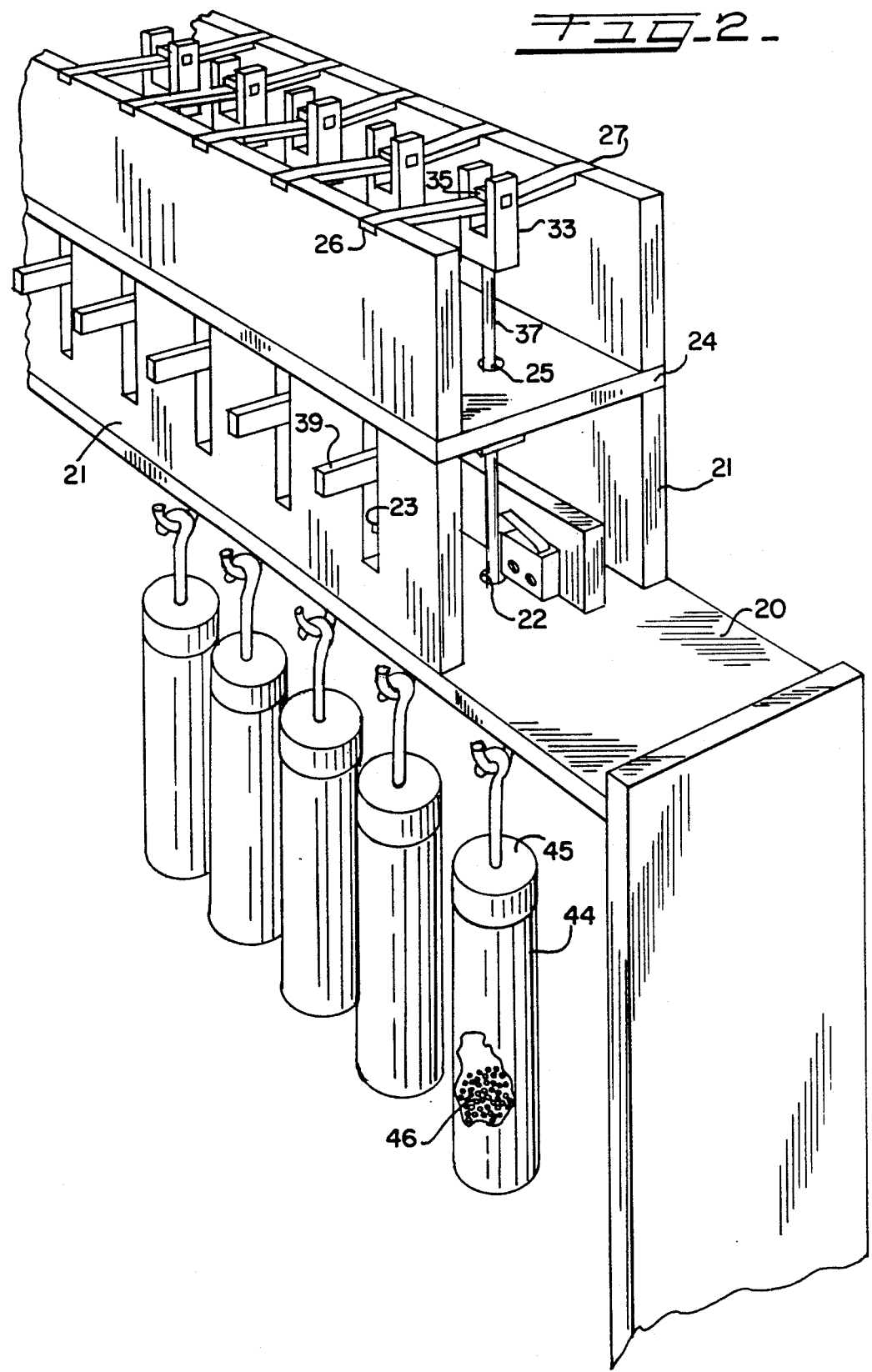
FIG. 2 shows a perspective view of an embodiment of the device of this invention.

FIG. 2 is a perspective view of the test article support of the device capable of multiple testing which comprises a horizontal platform 20 with two vertical panels 21 attached to the outer edges of the upper face of said platform. Said platform has at least one opening 22 along the center line and at least one of said panels has at least one opening 23. A horizontal member 24 connects the upper edges of said panels. Said member has at least one opening 25 vertically aligned with the opening in the horizontal platform. Vertical holders are connected to the outer edges of the upper face of said member. At the upper edges of said holders are channels 26 adapted to hold a test article 27. Stress is applied to the test article by means of the hanger assembly which comprises a frame 33 having a contact piece 35 which is in direct contact with the test article. Said contact piece preferably has a flat surface in contact with the test article. Attached to the bottom of said frame is a vertical connector 37 which passes through the openings 22 and 25. The connector is aligned so that it passes freely through the openings. A horizontal lever 39 is attached to said connector and aligned so as to extend through the opening 23 in the vertical panel. A weight is attached to the end of said connector opposite said frame thereby producing the load which stresses the test article. Although fixed weights can be used, it is preferable to use weights which can be easily and accurately varied so that they can be conveniently changed to exert a designated flexural stress on the article. The stress applied to the test article should not exceed its yield stress, i.e., the maximum stress a sample can withstand before it is permanently deformed. Yield stresses vary with different polymer materials. The weight can be a container filled with material of a known weight comprising a holder for the material 44 and a top 45 which is adapted to be removably connected to the end of said vertical connector opposite said frame. The material in the container 46 can be material which has been previously weighed such as lead shot.

In FIG. 3, an end-on view of an embodiment of the invention is shown. The horizontal lever 39 is attached to said vertical connector at a point where said lever extends through the openings 26 in the vertical panels. The horizontal lever is attached to the vertical connector in a manner such that a portion of said lever extends beyond the vertical plane of said connector to an extent that such an extension 41 is in vertical alignment with a switch 42. Said lever is located on said vertical connector at a point at which the extension 41 will not contact the switch 42 until the test article undergoes catastrophic cracking and fails completely. After the failure of the sample, the hanger assembly is supported by the horizontal member until the next sample is inserted.

The timer assembly is attached to the switch so that the time between the initial application of stress to the test article and the catastrophic cracking of said article can be measured.

The test articles used in the method of this invention can be formed by any convenient melt processing method such as compression molding, extrusion or injection molding. The preferred method is compression molding since it avoids imparting anisotropy to the test article. Typically, the test article is made by compression molding the polymer to be tested into a plaque. The plaque is cut into rectangular test articles of predetermined dimensions. Handling of the articles is minimized and the articles are wiped prior to testing. The amount of stress cracking agent applied to the test article is not critical. Typically, liquid or solid agents are applied to form a film of the agent on the underside of the test article. In the method of this invention, a stress cracking agent is applied to one side of the test articles which are then placed in the device of this invention. Stress is applied to the opposite side of the articles by means of the hanger assembly. The weight producing the stress is located below the plane of the test article. The time between the application of stress to the article and the displacement of the hanger assembly to catastrophic cracking of the article is measured. The failure time of the test article is recorded to the nearest 0.1 minute.

The stress applied in the method of this invention is sufficient to produce cracking within a convenient length of time and yet not greater than the yield stress of the polymer since this could alter the mechanism of stress crack failure. The range of applied stress will be determined by the polymer material being tested. In general, a flexural stress level from about 500 psi to about 3000 psi can be used, preferably about 2000 psi and most preferably about 1550 psi. When testing several samples of a particular polymer material, the ESCR can be measured in terms of a parameter, $F_{50}$, which is obtained by averaging the logarithms of the individual failure times and then taking the antilogarithm of this average. This method is preferred because it can be applied to any number of samples in a given test cycle. A convenient method of testing several samples is to measure the failure time of the first, third or fifth test article among ten samples to predict the ESCR of the material. For a rapid method of determining a characteristic ESCR, the failure time of the third test article to fail out of ten being tested can be used. Testing is performed at a nearly constant temperature since variations in temperature will cause changes in the failure times. Failure times tend to decrease as the temperature is increased. The method of this invention is preferably performed at the temperature range of about 71° F. (21.7° C.) to about 75° F. (23.9° C.), most preferably about 73.4° F. (23° C.). The temperature and humidity can be monitored during testing by a thermograph which records any fluctuations.

The method of this invention can be used for measuring the ESCR of articles of amorphous polymeric materials such as polystyrene, acrylonitrile-butadiene-styrene copolymers, polycarbonates and blends of polystyrene such as polystyrene/polyphenylene oxide blends. The preferred resins are high impact polystyrene (HIPS), acrylonitrile-butadiene-styrene copolymers and rigid polyvinyl chlorides.

Among the advantages associated with the method and device of this invention is the fact that it is convenient in both size and mode of operation. When compared to the devices of the prior art, there is a minimum number of working components. The hanger assembly is easily positioned on the test article which has been marked with the designated stress point. Therefore, the point of stress application can be accurately repeated on different samples. The amount of test material needed is very small and yet the method and device is sensitive to small changes in the ESCR. The displacement of the hanger assembly can be detected by any convenient means such as sound or visual detection. However, the device is readily automated by means of a micro switch to detect the vertical displacement of the hangar assembly and an automatic timer which can record the time elapsed between the application of stress and sample cracking. Therefore, the test need not be dependent upon an operator's vision and reaction time since the failure times will be automatically recorded upon displacement of the hanger assembly. Having the weight located below the test article eliminates the need for additional components to maintain the weight on a fixed path. The effect of friction as the weight moves is eliminated since the assembly and weight hang freely, suspended only by the test article itself.

The following example is given for the purpose of further illustrating the present invention and is not intended in any way to limit the scope of the invention.

EXAMPLE

Ten test specimens were prepared in the following manner: High impact polystyrene resin was placed in a mold chase and a compression molded plaque was then prepared by molding the resin at 200° C. for 2 minutes under 2 tons of pressure and 5 minutes under 10 tons of pressure. The platens of the press were then water cooled for 10 minutes at a cooling rate of approximately 15° C./min before removing the mold chase. Ten rectangular test specimens having dimensions of 2.5 inches by 0.250 inch by 0.060 inch were die cut from the plaque. The specimens were sanded on each long edge and the burrs on these edges were then removed using long continuous strokes of a fresh razor blade. Handling of the sample surfaces was minimized in order to avoid getting finger grease and oil on the specimens. After sanding and deburring, the specimens were carefully wiped clean with tissue paper.

Testing was performed in an environment is controlled to 73.4° F. (23° C.) as closely as possible. A thermograph was used to monitor the ambient temperature during testing. Each specimen was numbered on one end using marking pen. The width and thickness at the center of each specimen was measured to the nearest 0.0001 inch using a micrometer. The weights were placed on end of the connecters and the timers were set to zero. A cotton swab was used to apply a film of margarine to the underside of each specimen. The margarine was kept in a freezer at 0° C. until ½ hour before use and was allowed to come to the temperature of the test environment before application to the specimens. The specimen was then set in the channel underneath the contact piece of the hanger assembly. The timer started automatically when the assembly was raised onto the sample.

The $F_{50}$ value was calculated by averaging the logarithms of the individual failure times and then taking the anti-log of this average.

TABLE 1

| | | Stress level: 1550 psi | | |
|---|---|---|---|---|
| Specimen Number | Width (in) | Thickness (in) | Test Wt. (g) | Failure Time (min) |
| 1 | 0.2490 | 0.0590 | 181.4 | 356.5 |
| 2 | 0.2482 | 0.0579 | 173.6 | 320.4 |
| 3 | 0.2485 | 0.0582 | 175.8 | 311.4 |
| 4 | 0.2491 | 0.0600 | 188.2 | 310.5 |
| 5 | 0.2484 | 0.0598 | 186.3 | 373.3 |
| 6 | 0.2594 | 0.0570 | 168.6 | 263.0 |
| 7 | 0.2500 | 0.0600 | 189.0 | 365.5 |
| 8 | 0.2484 | 0.0600 | 187.7 | 274.4 |
| 9 | 0.2485 | 0.0567 | 166.1 | 261.7 |
| 10 | 0.2495 | 0.0570 | 168.7 | 282.8 |

$F_{50} = 309.4$ min

What is claimed is:

1. A method for determining the environmental stress crack resistance of a plastic article comprising
   (1) applying a chemical stress cracking agent to one side of said article,
   (2) applying a load to the opposite side of said article by means of a weight located below the article and below a horizontal plane defined by said opposite side of the article,
   (3) measuring the time between the application of said load and the failure of said article due to cracking.
2. The method of claim 1 wherein said article comprises a thermoplastic polymer.
3. The method of claim 2 wherein said article is a rectangular molded plaque having at least two flat planar surfaces.
4. The method of claim 2 wherein the thermoplastic polymer is selected from the group consisting of polystyrene, acrylonitrile-butadiene-styrene copolymers, polycarbonates, polyvinyl chloride, and polystyrene/-polyphenylene oxide blends.
5. The method of claim 4 wherein said polymer is selected from the group consisting of high impact polystyrene, acrylonitrile-butadiene-styrene copolymers and polyvinyl chloride.
6. The method of claim 1 wherein said stress cracking agent is selected from the group consisting of fats, oils, greases, and organic solvents.
7. The method of claim 6 wherein said stress cracking agent comprises vegetable oil.
8. The method of claim 6 wherein said stress cracking agent comprises margarine.

* * * * *